United States Patent
Saito et al.

(10) Patent No.: US 6,593,088 B1
(45) Date of Patent: Jul. 15, 2003

(54) REVERSIBLE PHOTOCOUPLING NUCLEIC ACID AND PHOSPHOROAMIDITE

(75) Inventors: Isao Saito, Kyoto (JP); Kenzo Fujimoto, Shiga (JP); Shigeo Matsuda, Osaka (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/830,401
(22) PCT Filed: Aug. 24, 2000
(86) PCT No.: PCT/JP00/05715
  § 371 (c)(1),
  (2), (4) Date: Jun. 28, 2001
(87) PCT Pub. No.: WO01/16151
  PCT Pub. Date: Mar. 8, 2001

(30) Foreign Application Priority Data

Aug. 27, 1999  (JP) ............................................ 11-240685

(51) Int. Cl.[7] .......................... C12Q 1/68; C07H 21/00
(52) U.S. Cl. .......................... 435/6; 536/23.1
(58) Field of Search .............................. 536/23.1, 28.5, 536/24.5, 24.1; 435/6; 548/266.2

(56) References Cited

U.S. PATENT DOCUMENTS 5,767,264 A * 6/1998 Otvos et al. ................ 536/24.5

FOREIGN PATENT DOCUMENTS

| EP | 324616 | | 7/1989 |
|----|--------|---|--------|
| EP | WO 94/17094 | * | 1/1993 |
| JP | 11-29591 | | 2/1999 |

OTHER PUBLICATIONS

S. G. Rahim et al., Synthesis and biological properties of 2'–deoxy–5–vinyluridine and 2'deoxy–5–vinylcytidine, Nucleic Acids Research, vol. 10, No. 17, 1987, pp. 5285–5295.*

Fujimoto Kenzo et al., "Template–Directed Photoreversible Ligation of Deoxyoligonucleotides via 5–Vinyldeoxyuridine", J. Am. Chem. Soc., vol. 122, No. 23, Jun. 14, 2000, pp. 5646–5647.

S. G. Rahim et al., "Synthesis and Biological Properties of 2'–deoxy–5–vinyluridine and 2'–deoxy–5–vinylcytidine", Nucleic Acids Research, vol. 10, No. 17, 1982, pp. 5285–5295.

* cited by examiner

Primary Examiner—Sean McGarry
Assistant Examiner—Janet Epps Ford
(74) Attorney, Agent, or Firm—Wenderoth, Lind & Ponack, L.L.P.

(57) ABSTRACT

As a novel technique, which gives selective photoligation in high yield and enables ligated site-specific photocleavage, as well as free and reversible control of photoligation and photocleavage, a reversible photoligating nucleic acid of the following formula (1):

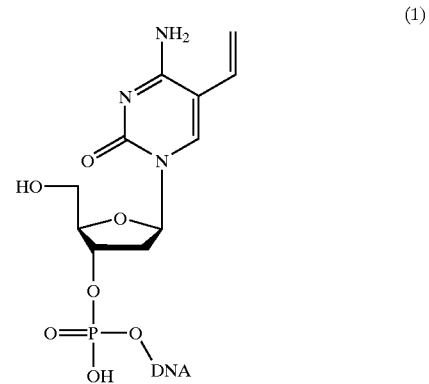

(1)

is used to control photoligation and photocleavage to and from biofunctional polymers freely.

4 Claims, 1 Drawing Sheet

REVERSIBLE PHOTOCOUPLING NUCLEIC ACID AND PHOSPHOROAMIDITE

BACKGROUND OF THE INVENTION

1. Field of the Invention

The present invention relates to reversible photoligating nucleic acids and phosphoramidites. More specifically, the present invention relates to a novel reversible photoligating nucleic acid which can be useful in its application to antisense DNA, antigene DNA, photogenetic diagnostic therapy, and in the analysis of DNA-protein interaction and the like, and can be used to control the formation and specific cleavage of ligation structures in biofunctional molecules using light; the present invention also relates to phosphoramidites useful for the synthesis of such nucleic acids, as well as methods of photoligation and photocleavage wherein such nucleic acids are used.

2. Description of the Related Art

It has been known that controlling the ligation and local cleavage between DNAs, RNAs, PNAs and proteins is important in determining biofunctions and the mechanism of bioactivities, as well as in creating bioactive substances.

For example, controlling the formation and the cleavage of the ligation structures of DNA-DNA, DNA-RNA, DNA-PNA or DNA-protein is very important in elucidating antisense DNAs, antigene DNAs, and genetic diagnostic therapy, and in determining the interactions between DNA-protein, as well as in controlling the structure of biomolecules accordingly.

Therefore, many means for ligation and cleavage have been studied, and methods involving photoirradiation are being investigated, as well.

However, the methods reported so far have problems such as the lowness of ligation product yield of about 40%, and the generation of various by-products. Further, examples of methods wherein the ligated sites are specifically cleaved have not been known.

Accordingly, the object of the present invention is to provide solutions to the above-described problems of the conventional methods, and to provide a novel technical means that gives selective high ligation product yield and selective photocleavage of the ligated site, and enables the free and reversible control of photoligation and photocleavage.

SUMMARY OF THE INVENTION

The present invention provides, as a means to solve the aforesaid problems, firstly, a reversible photoligating nucleic acid represented by the following formula (1):

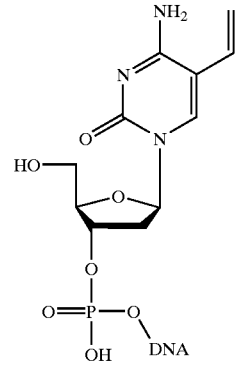

Also, secondly, a phosphoroamidite represented by the following formula (2):

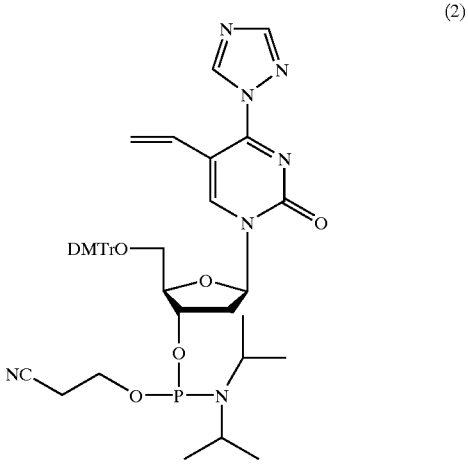

is provided.

Further, the present invention provides, thirdly, a method of photoligation, wherein a system containing the above reversible photoligation nucleic acid and a biofunctional polymer is irradiated to form a ligation structure. Fourthly, a method of photocleavage, wherein the ligated structure formed between a reversible photoligating nucleic acid and a biofunctional polymer is cleaved by the irradiation of light with short wavelength is provided.

By irradiating the above-described reversible photoligating nucleic acid of the present invention, i.e. a DNA containing photoligating nucleoside, 1) the ligation and cleavage of DNA-DNA, DNA-RNA, DNA-PNA and DNA-protein is enabled, and uses in a) antisense DNA, b) antigene DNA, c) photogenetic diagnostic therapy, and d) analysis of DNA-protein interaction may be developed.

Furthermore, according to the present invention, high ligation products yield of 95% or higher is obtained, and the ligated site-specific cleavage by irradiation is also enabled.

DESCRIPTION OF THE PREFERRED EMBODIMENTS

Figure 1:
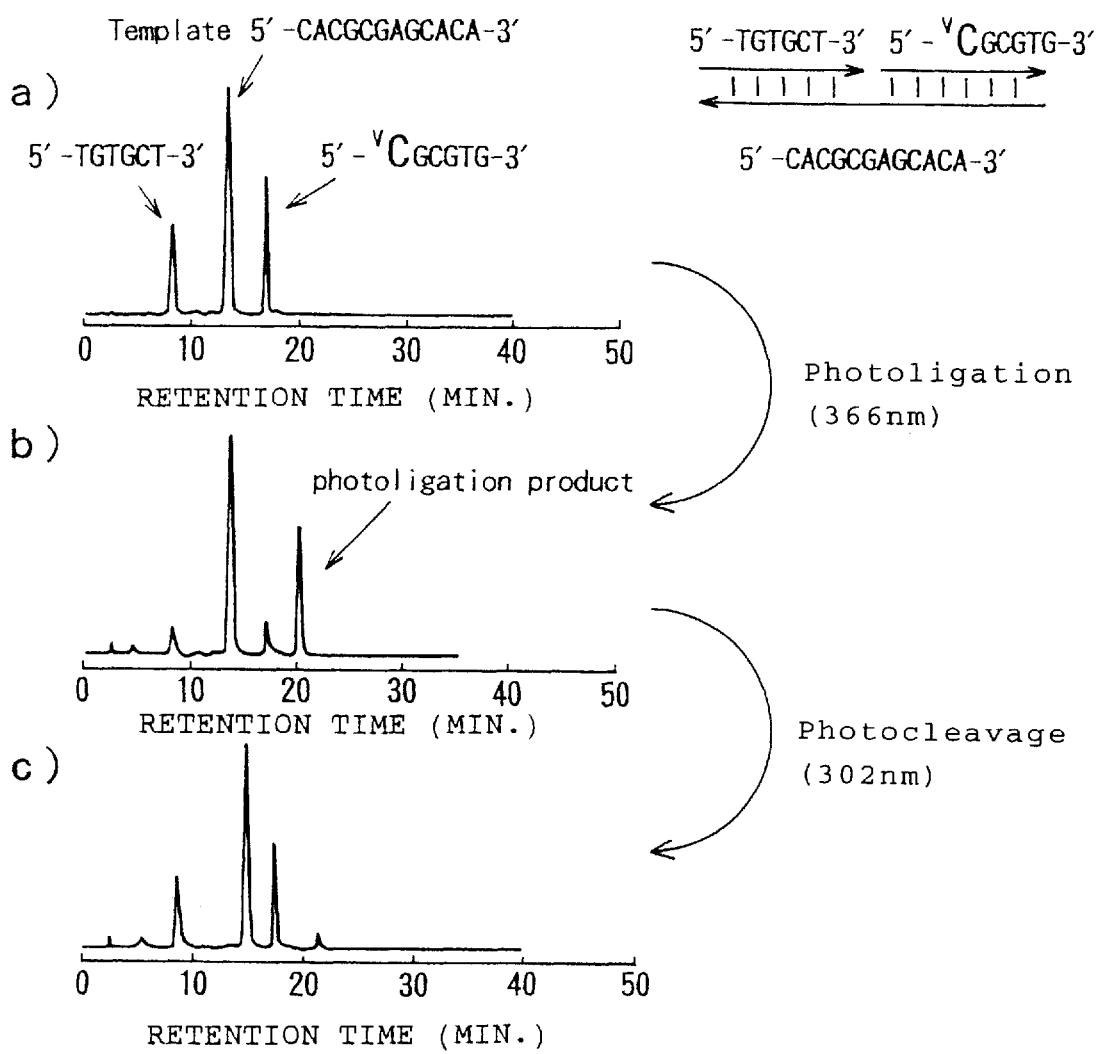
FIG. 1 shows an absorption spectrum exemplifying reversible photoligation and photocleavage reaction. The nucleic acid sequences, 5'-CACGCGAGCACA-3', 5'-TGTGCT-3', 5'-VCGCGTG-3', set forth in the Figure correspond to SEQ ID Nos: 1, 2 and 3, respectively, of the Sequence Listing.

The present invention comprises the characteristics described above; the best mode for carrying out the invention is described below.

The reversible photoligating nucleic acid of the above-described formula (1), i.e. a DNA containing photoligating nucleoside, of the present invention, has a characteristic structure comprising a vinyl group at the 5-position of the pyrimidinering. The presence of the vinyl group in the structure makes the control of ligation or cleavage with its pairing biofunctional polymer such as DNA, RNA, PNA or protein using light possible. The reversible photoligating nucleic acid may also be referred to as a vinylcytosine-containing functional nucleic acid. The reversible photoligating nucleic acid may also comprise other acceptable substituents in the pyrimidine ring and the nucleoside region; further, the amino group (NH$_2$) and the hydroxyl group (OH) may be protected by any permissible protecting group. The present invention also encompasses derivatives of the nucleic acid.

The photoligating nucleic acid of the present invention, represented by the above-described formula (1), may be easily synthesized by, for example, the following route, via a phosphoramidite represented by the above-described formula (2).

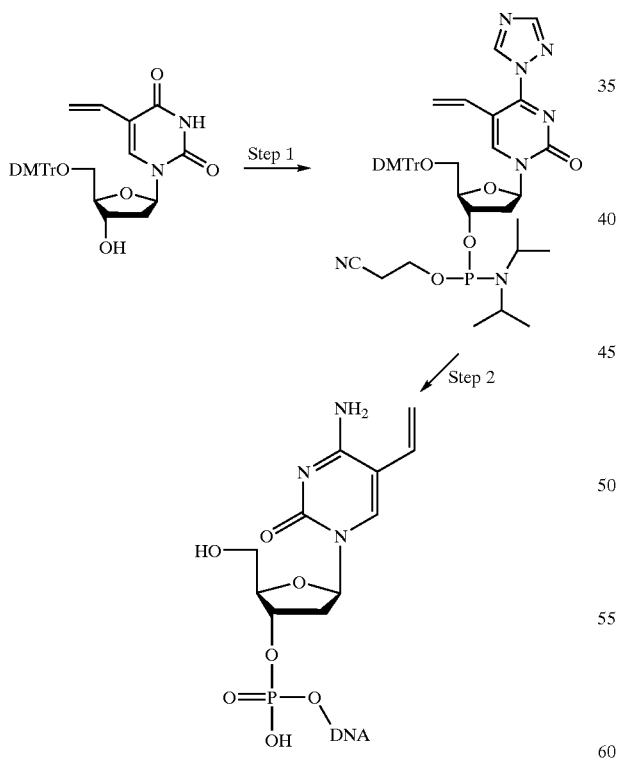

In step 1, for example, to a 5-vinyldeoxyuridine DMTr, a phosphitylating reagent is reacted to form a vinylcytosineamidite precursor, which is then reacted with 1, 2,4-triazol. In this case, examples of phosphitylating reagents include the following:

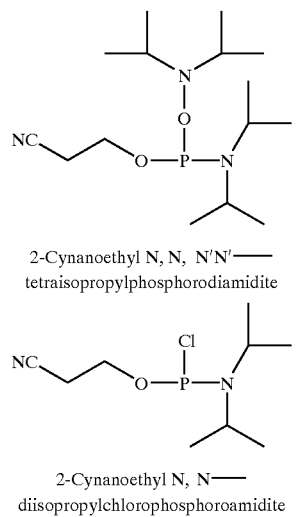

2-Cynanoethyl N, N, N'N'—tetraisopropylphosphorodiamidite

2-Cynanoethyl N, N—diisopropylchlorophosphoroamidite

Further, in step 2, DNA oligomers may be synthesized by a solid phase synthesis in a DNA synthesizer.

Photoligation is enabled by photoirradiation under the presence of biofunctional polymers such as DNA, RNA, PNA or protein, to which the nucleic acid is ligated. On the other hand, a photocleavage may be performed as a ligated site-specific cleavage, by irradiating light with shorter wavelength. For example, photoligation may be performed by photoexcitation at a wavelength longer than 330 nm, while photocleavage may be performed by photoexcitation at a wavelength shorter than 320 nm.

The method of photoirradiation, may be chosen from various means, an example being the use of a trans-illuminator.

The present invention is described in more detail through the following examples. However, the examples are merely illustrative in nature and serve as representative examples of the preferred embodiments. Other examples within the scope of the claims are also possible. Thus, the following examples should not be construed to narrow the spirit and scope of the claims.

EXAMPLES

Example 1

Synthesis

As a reversible photoreactive nucleic acid of the present invention, a functional nucleic acid containing vinylcytosine was synthesized, following steps 1 and 2 of the above-described reaction scheme.

(a) Step 1

To a solution of 5-vinyldeoxyuridine DMTr (166 mg, 0.298 mmol) in CH$_3$CN, 2.0 ml of a solution of a phosphitylating reagent (98.0 μL, 0.309 mmol) and 0.5 M tetrazol in CH$_3$CN (2.0 mL) was added. The reaction mixture was stirred for 1.0 hour, then extracted, after which the organic phase was dried and boiled with CH$_3$CN to give a vinylcytosineamidite precursor (228 mg). Next, to a CH$_3$CN solution of phosphorus trichloride (0.32 g, 2.10 mmol) and 1,2,4-triazol (0.667 g, 9.676 mmol), the vinylcytosineamidite precursor was added in three parts at 0° C. and stirred for 3 hours. Then, extraction was performed; the organic phase obtained was dried and boiled with CH$_3$CN to give 95.7 mg (0.118 mmol) of vinylcytosineamidite at a yield of 75%.

Table 1

$^{1}$HNMR (400 MHz, CDCl$_3$) d 2.21 (ddd, J=12.1 Hz, J=7.4 Hz, J=6.3 Hz, 1H, H-2'b), 2.35 (ddd, J=12.1 Hz, J=6.1 Hz, J=3.1 Hz, 1H, H-2'a), 2.95 (dd, J=10.6 Hz, J=3.4 Hz, 1H, H-5'), 3.38 (dd, J=10.6 Hz, J=3.4 Hz, 1H, H-5'), 3.71 (s, 6H, OCH$_3$×2), 3.90–3.99 (m, 1H, H-4'), 4.45–4.48 (m, 3H, H-3'), 4.86(dd,J=10.2 Hz, 2.0 Hz, 1H, vinyl trans), 5.60–5.73(m, 1H, vinyl cis. H-1'), 6.29 (dd, J=7.4 Hz, J=6.1 Hz, 1H, H-1'), 6.73–6.77(m, 4H, H-b to OCH$_3$×4), 7.17–7.28 (m, 9H, phenyl), 7.29–7.32(m, 1H, C$\underline{\text{H}}$=CH$_2$), 7.58(s, 1H, H-6), 8.23 (bs, 1H, NH). $^{31}$PNMR (CDCl$_3$, 85% - H$_3$PO$_4$ in D$_2$O ext. 0 ppm) d 149.811 & 150.386 (diastereomer of the products).

(b) Step 2

The CH$_3$CN solution of vinylcytosine amidite (0.1 M, 3 mL) obtained in step 1 was subjected to an automated DNA synthesizer, and DNA oligomers were synthesized according to conventional solid phase synthesis methods, excised, deprotected and purified by high-performance liquid chromatography.

The compound obtained was identified by molecular weight determination through an ESI-TOF method.

(5'-VCGCGTG-3'(SEQ ID No: 3), 20 mM) in the presence of a template oligomer (5'-CACGCGAGCACA-3'(SEQ ID No: 1), 25 mM), and irradiated in 500 mM of cacodylic acid buffer (50 mM, pH7.0) at 366 nm using a transilluminator. Photoligation of the oligomers occurred with a yield of 90% or higher (FIGS. 1a) and b)).

Next, the solution was irradiated at 302 nm using a transilluminator. The oligomer was successfully photocleaved almost quantitatively (see FIGS. 1b) and c)).

The molecular weight of 5'-VCGCGTG-3'(SEQ ID No:3) was determined by ESI-TOFF. Results are shown in the following Table 2.

Table 2

ESI-TOFF mass calcd. for C$_{80}$H$_{75}$N$_{23}$O$_{35}$P$_5$(M-H), 1832.36; found, 1832.34

As described in detail above, the present invention provides a novel technique, which enables high ligation product yield, specific photocleavage of ligated-sites, and free and reversible control of photoligation and photocleavage.

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence:
      SYNTHESIZED DNA OLIGOMER

<400> SEQUENCE: 1
cacgcgagca ca                                                      12

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence:
      SYNTHESIZED DNA OLIGOMER

<400> SEQUENCE: 2 tgtgct                                                              6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence:
      SYNTHESIZED DNA OLIGOMER

<400> SEQUENCE: 3 cgcgtg                                                              6
```

Example 2

Reversible Photoligation and Photocleavage

The target oligomer (5'-TGTGCT-3'(SEQ ID No: 2), 20 mM) was mixed with a vinylcytosine-containing oligomer

What is claimed is:

1. A phosphoramidite represented by the following formula (2):

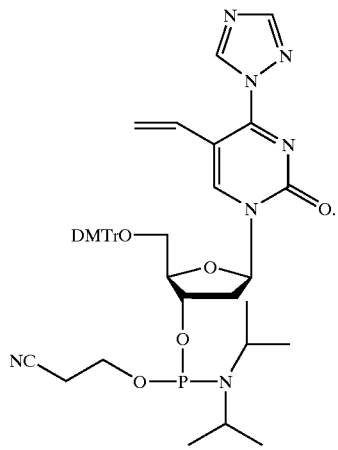

(2)

2. A method of photoligation comprising irradiating a system comprising a reversible photoligating nucleic acid represented by the following formula (1):

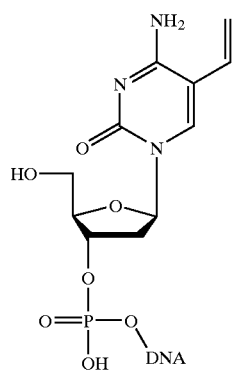

(1)

and a biofunctional polymer to form a ligation structure.

3. A method of photocleaving comprising irradiating a ligation structure comprising a reversible photoligating nucleic acid represented by the following formula (1):

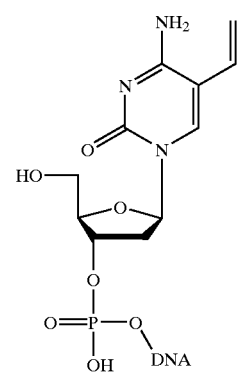

(1)

and a biofunctional polymer at a wavelength of shorter than 320 nm to cleave the litigation structure.

4. The method of photocleaving according to claim 3, wherein litigation structure is irradiated at a wavelength 20 nm or more shorter than the wavelength at which photoligation occurs.

* * * * *